(12) United States Patent
Pastan et al.

(10) Patent No.: US 7,368,110 B2
(45) Date of Patent: May 6, 2008

(54) ANTIBODIES, INCLUDING FV MOLECULES, AND IMMUNOCONJUGATES HAVING HIGH BINDING AFFINITY FOR MESOTHELIN AND METHODS FOR THEIR USE

(75) Inventors: Ira H. Pastan, Potomac, MD (US); Partha S. Chowdhury, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 257 days.

(21) Appl. No.: 10/973,718

(22) Filed: Oct. 25, 2004

(65) Prior Publication Data

US 2005/0214304 A1 Sep. 29, 2005

Related U.S. Application Data

(62) Division of application No. 09/581,345, filed as application No. PCT/US98/25270 on Nov. 25, 1998, now Pat. No. 6,809,184.

(60) Provisional application No. 60/067,175, filed on Dec. 1, 1997.

(51) Int. Cl.
*A61K 39/395* (2006.01)
(52) U.S. Cl. .................................. 424/133.1
(58) Field of Classification Search .................. None
See application file for complete search history.

(56) References Cited

U.S. PATENT DOCUMENTS

| 5,320,956 | A | * | 6/1994 | Willingham et al. | ...... 530/388.8 |
| 5,498,698 | A | | 3/1996 | Yamaguchi et al. | |
| 5,723,318 | A | | 3/1998 | Yamaguchi et al. | |
| 5,747,654 | A | | 5/1998 | Pastan et al. | |
| 6,083,502 | A | * | 7/2000 | Pastan et al. | ............ 424/178.1 |
| 6,153,430 | A | | 11/2000 | Pastan et al. | |
| 7,081,518 | B1 | * | 7/2006 | Pastan et al. | ............ 530/387.3 |

FOREIGN PATENT DOCUMENTS

| WO | WO 92 07081 | 4/1992 |
| WO | WO 9207081 | 4/1992 |
| WO | WO 9725068 A2 * | 7/1997 |
| WO | WO 97 34634 | 9/1997 |

OTHER PUBLICATIONS

Chowdhury et al ((J. Mol. Biol 281:917-928, 1998).*
Brinkman U et al., *International Journal of Cancer*, (May 16, 1997) 71 (4) 638-44.
Chang , K. et al., *Cancer Research* (Jan 1, 1992) 52 (1) 181-6.
Kuby, Janis *W.H. Freeman and Company New York, United States of America*, (1994, pp. 136-134).
Heidelberg, *Database EMBL (EMPRO) EMBL* (Mar. 10, 1998).
Chowdhury, P.S. et al., *Proceedings of the National Academy of Sciences of the United States of America*, (Jan. 20, 1998) 95 (2) 669-74.
Chowdhury, P.S. et al., *Molecular Immunology*, (Jan. 1997) 34 (1).
Chowdhury, P.S. et al., *Journal of Molecular Biology*, (Sep. 4, 1998) 281 (5) 917-28.
Yamaguchi, Nozomi et al.; "A Novel Cytokine Exhibiting Megakaryocyte Potentiating Activity From a Human Pancreatic Tumor Cell Line HPC-Y5"; 1994, *The Journal of Biological Chemistry*, vol. 269, No. 2, pp. 805-808.

* cited by examiner

*Primary Examiner*—Brandon Fetterolf
(74) *Attorney, Agent, or Firm*—Townsend and Townsend and Crew LLP

(57) ABSTRACT

Mesothelin ins a differentiation antigen present on the surface of ovarian cancers, mesotheliomas and several other types of human cancers. Because among normal tissues, mesothelin is only present on mesothelial cells, it represents a good target for antibody mediated delivery of cytotoxic agents. The present invention is directed to anti-mesothelin antibodies, including Fv molecules with particularly high affinity for mesothelin, and immunoconjugates employing them. Also described are diagnostic and therapeutic methods using the antibodies. The anti-mesothelin antibodies are well-suited for the diagnosis and treatment of cancers of the ovary, stomach, squamous cells, mesotheliomas and other malignant cells expressing mesothelin.

11 Claims, 5 Drawing Sheets

SEQUENCE LISTING

```
<160> NUMBER OF SEQ ID NOS: 9

<210> SEQ ID NO 1
<211> LENGTH: 723
<212> TYPE: DNA
<213> ORGANISM: Artificial Sequence
<220> FEATURE:
<223> OTHER INFORMATION: Description of Artificial Sequence:SS scFv

<400> SEQUENCE: 1
atgcaggtac aactgcagca gtctgggcct gagctggaga agcctggcgc ttcagtgaag      60
atatcctgca aggcttctgg ttactcattc actggctaca ccatgaactg ggtgaagcag     120 agccatgaa  agagccttga gtggattgga cttattactc cttacaatgg tgcttctagc     180
tacaaccaga agttcagggg caaggccaca ttaactgtag acaagtcatc cagcacagcc     240
tacatggacc tcctcagtct gacatctgaa gactctgcag tctatttctg tgcaaggggg     300
ggttacgacg ggagggtttt tgactactgg ggccaaggga ccacggtcac cgtctcctca     360
ggtgtaggcg gttcaggcgg cggtggctct ggcggtggcg gatcggacat cgagctcact     420
cagtctccag caatcatgtc tgcatctcca ggggagaagg tcaccatgac ctgcagtgcc     480
agctcaagtg taagttacat gcactggtac cagcagaagt caggcacctc ccccaaaaga     540
tggatttatg acacatccaa actggcttct ggagtcccag gtcgcttcag tggcagtggg     600
tctggaaact cttactctct cacaatcagc agcgtggagg ctgaagatga tgcaacttat     660
tactgccagc agtggagtgg ttaccctctc acgttcggtg ctgggacaaa gttggaaata     720
aaa                                                                    723

<210> SEQ ID NO 2
<211> LENGTH: 1917
<212> TYPE: DNA
<213> ORGANISM: Pseudomonas aeruginosa
<220> FEATURE:
<223> OTHER INFORMATION: Pseudomonas aeruginosa exotoxin A CDS
```

<400> SEQUENCE: 2

```
atgcacctga tacccattg  atcccctg   gtcgccagcc tcggcctgct cgccggcggc    60
tcgtccgcgt ccgccgccga ggaagccttc gacctctgga acgaatgcgc caaagcctgc   120
gtgctcgacc tcaaggacgg cgtgcgttcc agccgcatga gcgtcgaccc ggccatcgcc   180
gacaccaacg gccagggcgt gctgcactac tccatggtcc tggagggcgg caacgacgcg   240
ctcaagctgg ccatcgacaa cgccctcagc atcaccagcg acggcctgac catccgcctc   300
gaaggcggcg tcgagccgaa caagccggtg cgctacagct acacgcgcca ggcgcgcggc   360
agttggtcgc tgaactggct ggtaccgatc ggccacgaga agccctcgaa catcaaggtg   420
ttcatccacg aactgaacgc cggcaaccag ctcagccaca tgtcgccgat ctacaccatc   480
gagatgggcg acgagttgct ggcgaagctg gcgcgcgatg ccaccttctt cgtcagggcg   540
cacgagagca acgagatgca gccgacgctc gccatcagcc atgccggggt cagcgtggtc   600
atggcccaga cccagccgcg ccgggaaaag cgctggagcg aatgggccag cggcaaggtg   660
ttgtgcctgc tcgacccgct ggacggggtc tacaactacc tcgcccagca acgctgcaac   720
ctcgacgata cctgggaagg caagatctac cgggtgctcg ccggcaaccc ggcgaagcat   780
gacctggaca tcaaacccac ggtcatcagt catcgcctgc actttcccga gggcggcagc   840
ctggccgcgc tgaccgcgca ccaggcttgc cacctgccgc tggagacttt cacccgtcat   900
cgccagccgc gcggctggga caactggag  cagtgcggct atccggtgca gcggctggtc   960
gccctctacc tggcggcgcg gctgtcgtgg aaccaggtcg accaggtgat ccgcaacgcc  1020
ctggccagcc ccggcagcgg cggcgacctg ggcgaagcga tccgcgagca gccggagcag  1080
gcccgtctgg ccctgaccct ggccgccgcc gagagcgagc gcttcgtccg cagggcacc   1140
ggcaacgacg aggccggcgc ggccaacgcc gacgtggtga gcctgacctg cccggtcgcc  1200
gccggtgaat gcgcgggccc ggcggacagc ggcgacgccc tgctggagcg caactatccc  1260
actggcgcgg agttcctcgg cgacggcggc gacgtcagct tcagcacccg cggcacgcag  1320
aactggacgg tggagcggct gctccaggcg caccgccaac tggaggagcg cggctatgtg  1380
ttcgtcggct accacggcac cttcctcgaa gcggcgcaaa gcatcgtctt cggcggggtg  1440
cgcgcgcgca gccaggacct cgacgcgatc tggcgcggtt tctatatcgc cggcgatccg  1500
gcgctggcct acggctacgc ccaggaccag gaacccgacg cacgcggccg gatccgcaac  1560
ggtgccctgc tgcgggtcta tgtgccgcgc tcgagcctgc cgggcttcta ccgcaccagc  1620
ctgaccctgg ccgcgccgga ggcggcgggc gaggtcgaac ggctgatcgg ccatccgctg  1680
ccgctgcgcc tggacgccat caccggcccc gaggaggaag cgggcgcct  ggagaccatt  1740
ctcggctggc cgctggccga gcgcaccgtg gtgattccct cggcgatccc caccgacccg  1800
cgcaacgtcg gcgcgacct  cgacccgtcc agcatcccg  acaaggaaca ggcgatcagc  1860
gccctgccgg actacgccag ccagcccggc aaaccgccgc gcgaggacct gaagtaa     1917
```

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence:New G2 NdeI back primer

<400> SEQUENCE: 3

```
taagaaggag atatacatat gcaggtacaa ctgcagcagt ctggg              45
```

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:New G2 HindIII forward primer

<400> SEQUENCE: 4
gccctcggga cctccggaag cttttatttc aactttgtc cc        42

<210> SEQ ID NO 5
<211> LENGTH: 241
<212> TYPE: PRT
<213> ORGANISM: Artificial Sequence
<220> FEATURE:
<223> OTHER INFORMATION: Description of Artificial Sequence:SS scFv

<400> SEQUENCE: 5

```
Met Gln Val Gln Leu Gln Gln Ser Gly Pro Glu Leu Glu Lys Pro Gly
 1               5                  10                  15

Ala Ser Val Lys Ile Ser Cys Lys Ala Ser Gly Tyr Ser Phe Thr Gly
             20                  25                  30

Tyr Thr Met Asn Trp Val Lys Gln Ser His Gly Lys Ser Leu Glu Trp
         35                  40                  45

Ile Gly Leu Ile Thr Pro Tyr Asn Gly Ala Ser Ser Tyr Asn Gln Lys
     50                  55                  60

Phe Arg Gly Lys Ala Thr Leu Thr Val Asp Lys Ser Ser Ser Thr Ala
 65                  70                  75                  80

Tyr Met Asp Leu Leu Ser Leu Thr Ser Glu Asp Ser Ala Val Tyr Phe
                 85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Gly Val Gly Gly Ser Gly Gly Gly
        115                 120                 125

Gly Ser Gly Gly Gly Gly Ser Asp Ile Glu Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met His Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Gly Arg Phe Ser Gly Ser Gly Ser Gly Asn Ser Tyr Ser Leu Thr
        195                 200                 205

Ile Ser Ser Val Glu Ala Glu Asp Asp Ala Thr Tyr Tyr Cys Gln Gln
    210                 215                 220

Trp Ser Gly Tyr Pro Leu Thr Phe Gly Ala Gly Thr Lys Leu Glu Ile
225                 230                 235                 240

Lys
```

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:linker peptide connecting V-H and V-L in SS scFv

```
<400> SEQUENCE: 6

Gly Val Gly Gly Ser Gly Gly Gly Ser Gly Gly Gly Gly Ser
 1               5                  10                  15

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:peptide
      linker

<400> SEQUENCE: 7

Gly Gly Gly Ser
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:carboxyl
      terminus

<400> SEQUENCE: 8

Lys Asp Glu Leu
 1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:carboxyl
      terminus

<400> SEQUENCE: 9

Arg Glu Asp Leu
 1
```

ANTIBODIES, INCLUDING FV MOLECULES, AND IMMUNOCONJUGATES HAVING HIGH BINDING AFFINITY FOR MESOTHELIN AND METHODS FOR THEIR USE

CROSS-REFERENCES TO RELATED APPLICATIONS

This application is a divisional patent application of U.S. patent application Ser. No. 09/581,345, filed Sep. 27, 2000, now U.S. Pat. No. 6,809,184, which is, in turn, a U.S. national phase of International Patent Application No. PCT/US98/25270, filed Nov. 25, 1998, claiming priority to U.S. Provisional Patent Application No. 60/067,175, filed Dec. 1, 1997, all of which are incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

In many types of cancer cells, differentiation antigens are expressed. These antigens have been used as targets in cancer therapy. For example, CD19, CD20, CD22 and CD25 have successfully been used as targets in hematopoietic malignancies (Press, et al., *New Eng. J. Med.* 329:1219-1224 (1993); and Osterborg, et al., *J. Clin. Oncol.* 15:1567-1574 (1997)). However, this targeted cancer therapy has not been successful with solid tumors, in large part because the targeted antigens are also expressed in tissues from which the tumors arose. Thus, such targeted therapies kill healthy cells as well as the malignant cells.

In the United States, despite therapy, an estimated 15,000 women die of ovarian cancer each year. Although less common than ovarian cancer, mesotheliomas are known to be resistant to all chemotherapeutic agents and therefore have a high mortality rate. Because of the morbidity of these cancers, new therapeutic approaches to these malignancies are needed.

Common to ovarian, squamous cell and some stomach cancers as well as mesotheliomas is the expression of mesothelin on the cell surface (Chang, et al., *Cancer Res.* 52:181-186 (1992); Chang, et al., *J. Surgical Pathology* 16:259-268 (1992); and Chang, et al., *Nat'l Acad. Sci. USA* 93:136-140 (1996)). Mesothelin is a 40 kD GPI-linked glycoprotein antigen present on the surface of mesothelial cells. It is synthesized as a 69 kD precursor which is then proteolytically processed. The 30 kD amino terminus is secreted and has been termed megakaryocyte potentiating factor (Yamaguchi, et al., *J. Biol. Chem.* 269:805-808 (1994)). The 40 $k_D$ carboxyl terminus remains bound to the membrane as mature mesothelin (Chang, et al., *Nat'l Acad. Sci. USA* 93:136-140 (1996)). Unlike many cell surface antigens present on cancer cells, the membrane-bound form of mesothelin cannot be detected in the blood of cancer patients and is not shed by cultured cells into medium (Chang, et al., *Cancer Res.* 52:181-186 (1992)). In addition to malignant cells, mesothelin is also found on the cell surface of cells of mesothelial origin, including ovarian cancers. Because damage to cells in these tissues would not lead to life-threatening consequences, the presence of mesothelin on the surface of cancer cells makes it a promising candidate for targeted therapies.

Immunotoxins are antibodies directed against cell surface antigens joined to a toxic moiety. In the treatment of cancer, the antibody preferably is directed against a cell surface antigen expresser only on cancer cells. However, if the death of normal cells which also express the surface antigen is not more life-threatening than the existence of the malignancy, antibodies directed against cell surface antigens expressed on non-malignant cells can be used in cancer therapy. The toxic moiety of the immunotoxin can be any toxin that is not harmful to non-targeted cells at low concentrations after systemic administration. Such a toxin is the *Pseudomonas aeruginosa* exotoxin (PE). Previous studies with PE have demonstrated that the active portion of the protein is composed of domain II and III, both of which are located at the carboxyl end of the toxin.

The antibodies that target the immunotoxin can be polyclonal, monoclonal, or recombinant antibodies, such as chimeras or variable region fragments. If the antibody is non-recombinant, the immunotoxin must be formed by chemical conjugation of the antibody to the toxic moiety. If the antibody is produced recombinantly, the antibody can be joined to the toxin through chemical bonding or through recombinant fusion. In recombinant fusion, cDNA encoding the antibody is inserted, in frame, into a plasmid that already contains cDNA which encodes the toxin. Of course, the reverse could be done as well; the toxin cDNA can be inserted into a plasmid carrying cDNA which encodes the antibody.

Because of the potential large size of the immunotoxin, it is sometimes desired to join only a fragment of an antibody to the toxic moiety. Fab, Fab' and F(ab)$_2$ fragments can be made from polyclonal, monoclonal and chimeric antibodies and then joined to the toxin through chemical bonding.

Alternatively, a cDNA can be produced in which the variable regions of an antibody are connected to essential framework regions. These smaller antibodies are then secreted as double chain Fv antibodies or, if the heavy and light chain regions are joined either directly or through a peptide linker, as single chain Fv antibodies (scFv).

One method of creating a scFv is through phage display libraries made from splenic mRNA of mice immunized with an immunogen (Chowdhury, et al., *Mol. Immunol.* 34:9-20 (1997)). However, if a protein immunogen is naturally found in mammals but is recombinantly expressed in prokaryotes, the protein will not have the correct glycosylation pattern and may not have the correct conformation. Antibodies developed by the mouse in response to this immunogen may not recognize the protein in its native state. One solution to this problem is to immunize animals with the native protein made in mammalian cells, but purification from mammalian cells of sufficient amounts of some proteins, in particular cell surface proteins, may not be possible. Another solution, although not as common, is to immunize animals with cDNA which encodes the immunogen. The cDNA, under the control of an appropriate promoter, is introduced into the animal. After boosting injections and when the antibody titer reaches a maximum, the animals are sacrificed and the spleens removed to create the phage display library.

There is a need for better chemotherapeutic agents to control cancers such as ovarian cancer and mesotheliomas, both of which are rarely cured by currently available chemotherapies. The following disclosure describes such a chemotherapeutic agent.

BRIEF SUMMARY OF THE INVENTION

In one aspect, the present invention relates to an anti-mesothelin antibody with a dissociation constant of less than $3 \times 10^{-8}$ M and which specifically binds to mesothelin on the surface of cells. In one embodiment, the anti-mesothelin antibodies are a single chain antibody comprising a variable heavy chain region and a variable light chain region. In yet other embodiments, the CDRs of the antibody are as indicated in FIG. 1. In other embodiments, the antibody is linked to an effector molecule, for example, a detectable label or a therapeutic agent. In one embodiment, the therapeutic agent is a toxin, preferably Pseudomonas exotoxin A or cytotoxic fragments thereof.

In another embodiment of the invention, the antibody is produced by immunizing an animal with cDNA which encodes mesothelin, preparing a phage display library from the mRNA isolated from the spleen of the immunized animal, selecting for phage that specifically bind mesothelin with a dissociation constant of less than $3 \times 10^{-8}$ M and which binds to mesothelin expressed on the surface of cells, isolating the nucleic acid from the bound phage, introducing the nucleic acid into a cell which expresses the phage-derived-mesothelin antibody and isolating the antibody from the cell. It further is contemplated that the nucleic acid sequences which encode the anti-mesothelin antibody are fused in frame to nucleic acid sequences which encode for the toxic moiety.

In another aspect, the present invention relates to an immunoconjugate of an anti-mesothelin antibody with a dissociation constant of less than $3 \times 10^{-8}$ M and which specifically binds to mesothelin on the surface of cells and a therapeutic agent or a detectable label. In one embodiment, the anti-mesothelin antibody is a single chain antibody comprising a variable heavy chain region and a variable light chain region. In other embodiments, the CDRs of the antibody are as indicated in FIG. 1. In yet another embodiment, the variable heavy chain region and the variable light chain region are bonded through a linker peptide. In other embodiments, the therapeutic agent is a toxin, preferably Pseudomonas exotoxin A or cytotoxic fragments thereof. Particularly preferred is PE38. In yet other embodiments, the variable heavy chain region of the antibody is peptide bonded to the carboxyl terminus of the therapeutic agent or detectable label.

In another aspect, the present invention relates to expression cassettes encoding either a recombinant anti-mesothelin immunoconjugate or a recombinant anti-mesothelin antibody. In some embodiments, the antibody is a single chain Fv antibody comprising a variable heavy chain region and a variable light chain region. In yet other embodiments, the CDRs of the antibody are as indicated in FIG. 1. In some embodiments, the immunoconjugate comprises a detectable label. In other embodiments, the anti-mesothelin antibody is bonded to a therapeutic agent, preferably a toxin and more preferably a Pseudomonas exotoxin A or cytotoxic fragments thereof, and most preferably PE38.

In yet another aspect, the present invention relates to host cells comprising expression cassettes which encode recombinant immunoconjugates or anti-mesothelin antibodies. In some embodiments, the host cells comprise an anti-mesothelin single chain Fv antibody comprising a variable heavy chain region and a variable light chain region. In yet other embodiments, the CDRs of the antibody are as indicated in FIG. 1. In further embodiments, the variable heavy chain region and the variable light chain region are linked through a peptide linker. The immunoconjugate comprises either a detectable label or a therapeutic agent bonded to an anti-mesothelin scFv fragment. In preferred embodiments, the therapeutic agent is a toxin, more preferably Pseudomonas exotoxin A or cytotoxic fragments thereof, and most preferably PE38.

In yet another aspect, the present invention relates to a method for inhibiting the growth of a malignant cell which expresses mesothelin on its cell surface. The method comprises the steps of contacting the malignant cell with an effective amount of a recombinant immunoconjugate comprising a toxic peptide bonded to an anti-mesothelin antibody which has a dissociation constant of less than $3 \times 10^{-8}$ M and binds to mesothelin expressed on cell surfaces. In one embodiment, the anti-mesothelin antibody is a scFv antibody with a variable heavy chain region and a variable light chain region. In another embodiment, the CDRs of the antibody are as indicated in FIG. 1. In yet other embodiments, the variable heavy chain region and the variable light chain region are linked by a peptide linker. In some embodiments the toxic peptide is Pseudomonas exotoxin (PE) or a cytotoxic fragment thereof, preferably PE38. In one embodiment, the variable heavy chain region is peptide bonded at the carboxyl terminus of the toxin. In some embodiments, the malignant cell is contacted with the immunoconjugate in vivo. The malignant cell, for example, can be an ovarian, squamous, gastric cell or a mesothelioma.

In a further aspect, the present invention is directed to a method for detecting the presence of mesothelin in a biological sample. The method comprises the steps of contacting the biological sample with an anti-mesothelin antibody which has a dissociation constant of less than $3 \times 10^{-8}$ M and binds to mesothelin expressed on cell surfaces, and allowing the antibody to bind to mesothelin under immunologically reactive conditions, wherein detection of the bound antibody indicates the presence of the mesothelin. In one embodiment, the antibody is a scFv fragment comprising a variable heavy ($V_H$) region and a variable light ($V_L$) region. In yet other embodiments, the CDRs of the antibody are as indicated in FIG. 1. In another embodiment, the $V_H$ region and the $V_L$ region are linked through a peptide linker. In one embodiment, the antibody employed in the method is detectably labeled. In yet other embodiments, the antibody is conjugated to a toxic peptide and the presence of the immunoconjugate is detected by antibodies to the toxic peptide. In some embodiments, the method is performed in vivo in a mammal.

In yet a further aspect, the present invention is directed to pharmaceutical compositions comprising the immunoconjugates of this invention. In another aspect, the present invention is directed to kits which can be used to detect mesothelin on cell surfaces.

BRIEF DESCRIPTION OF THE DRAWINGS

FIG. 1 contains the amino acid sequence of SS scFv (SEQ ID NO:5) as deduced from its nucleotide sequence (SEQ ID NO: 1). In the scFv, $V_H$ is connected to $V_L$ by a linker peptide, GVGGSG$_4$SG$_4$S (SEQ ID NO:6). The framework regions and CDRs have been marked.

FIG. 2 demonstrates that phage displaying SS scFv bound specifically to mesothelin (a.a. 291-606) coated ELISA wells in a dose-dependent manner. Phage were exposed to wells coated with mesothelin, the p55 subunit of the IL-2 receptor, bovine serum albumin, streptavidin or uncoated wells. Bound phage were detected as described in the Examples section.

FIG. 3 shows that epitopes which bind SS scFv and K1 are different. Mesothelin-coated wells were incubated with various dilutions of SS scFv or K1 scFv phage in the presence or absence of isolated monoclonal K1 at 1 µg/mL. Bound phage were detected as mentioned in the Examples section.

FIG. 4 indicates the stability of SS scFv-PE38 at 37° C. SS scFv-PE38 (10 µg/mL) was incubated at 37° C. for up to 40.5 hrs. and then its cytotoxic activity was measured. The chart demonstrates the percentage of initial activity remaining after various periods of incubation.

FIG. 5 shows the antitumor effect of SS scFv-PE38 in nude mice. Groups of five animals were injected with $1.5 \times 10^6$ A431 K5 cells on day 0. Animals were treated intravenously on days 5, 7 and 9 with 2.6 µg (♦) or 4.3 µg (□) of SS scFv-PE38 in Dulbecco's-PBS (DPBS) containing 0.2% human serum albumin (HSA). Control groups received either the carrier alone (○) or 3 µg anti-Tac(scFv)-PE38 (●).

DETAILED DESCRIPTION OF THE INVENTION

I. Overview

Figure 1:
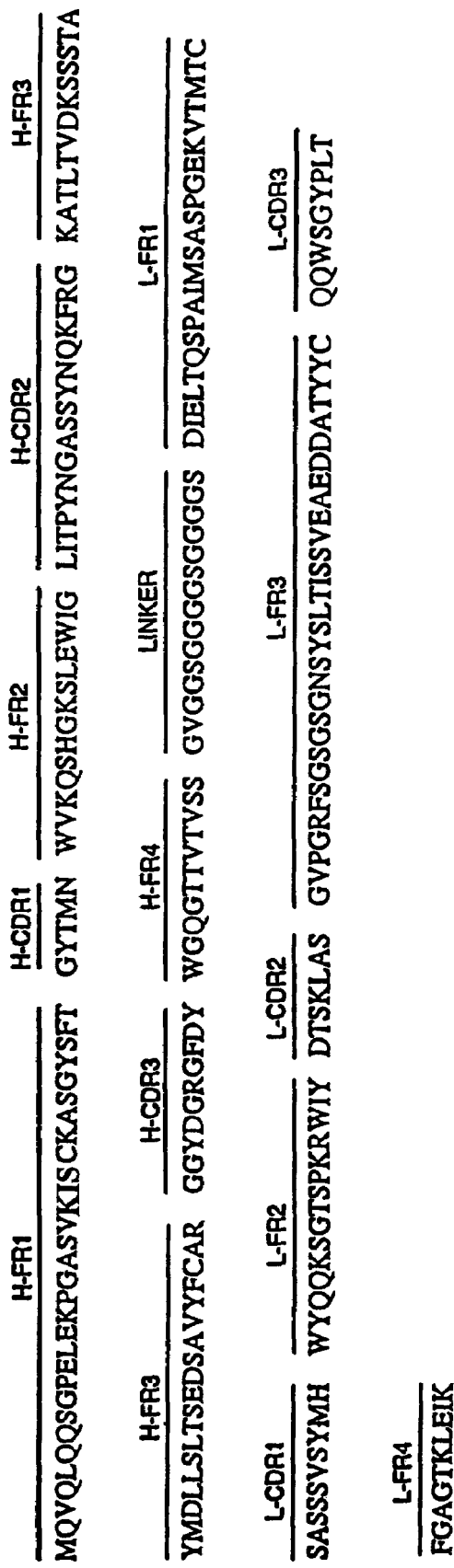
FIG. 1.

The present invention provides antibodies and immunoconjugates, preferably immunotoxins (IT), more preferably with *Pseudomonas* exotoxin A or cytotoxic fragments thereof as the toxic moiety, and most preferably with PE38 as the toxic moiety joined to an anti-mesothelin antibody, more preferably an Fv antibody, and most preferably a scFv antibody.

In a preferred embodiment, the antibody is a scFv. Many of the recombinant immunotoxins produced from constructs of scFv are one-third the size of IgG-toxin chemical conjugates and are homogeneous in composition. Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin (IT) interacts with non-target tissues and tissues that express very low levels of antigen.

Previous attempts to immunize mice with recombinant mesothelin resulted in antibodies that bound specifically to mesothelin on the surface of cells, but with low affinity. When animals were immunized with an expression plasmid comprising cDNA which encodes human mesothelin, antibodies which bound to cell surface mesothelin with surprisingly high affinity were obtained. It was found that multiple injections of cDNA were instrumental in achieving these unusually high titers. The difficulties in obtaining high affinity antibodies directed against mesothelin, the surprising activity of the antibodies towards cell surface mesothelin and the unique pharmacological properties afforded by the immunotoxins of the present invention make them highly effective therapeutic agents for treatment of cancers of the ovary, stomach, squamous cell cancers, mesotheliomas and other malignant cells which express mesothelin.

II. Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention which can be had by reference to the specification as a whole. Accordingly, the terms defined immediately below are more fully defined by reference to the specification in its entirety.

The term "mesothelin" includes reference to a mesothelin protein and fragments thereof which may be present on the surface of mammalian cells of a mammal such as rats, mice, and primates, particularly humans. The preferred nucleic acid and amino acid sequences of mesothelin are as described in PCT published application WO 97/25,068, U.S. application Ser. No. 08/776,271 and U.S. Provisional Application 60/010,166, all incorporated herein by reference. In addition, see, Chang, K. & Pastan, I., *Int. J Cancer* 57:90 (1994); Chang, K. & Pastan, I., *Proc. Nat'l Acad. Sci USA* 93:136 (1996); Brinkmann U., et al., *Int. J. Cancer* 71:638 (1997); and Chowdhury, P. S., et al., *Mol. Immunol.* 34:9 (1997), each of which is incorporated herein by reference. Mesothelin also refers to mesothelin proteins or peptides which remain intracellular as well as secreted and/or isolated extracellular protein.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments (See, U.S. Ser. No. 08/077,252, incorporated herein by reference), or pFv fragments (See, U.S. Provisional Patent Applications 60/042,350 and 60/048,848, both of which are incorporated herein by reference.). The term "antibody" also includes antigen binding forms of antibodies (e.g., Fab', F(ab')$_2$, Fab, Fv and rIgG. See also, Pierce Catalog and Handbook, 1994-1995 (Pierce Chemical Co., Rockford, Ill.).

An antibody immunologically reactive with a particular antigen can be generated by recombinant methods such as selection of libraries of recombinant antibodies in phage or similar vectors. See, e.g., Huse, et al., *Science* 246:1275-1281 (1989); Ward, et al., *Nature* 341:544-546 (1989); and Vaughan, et al., *Nature Biotech.* 14:309-314 (1996).

Typically, an immunoglobulin has a heavy and light chain. Each heavy and light chain contains a constant region and a variable region. Light and heavy chain variable regions contain a "framework" region interrupted by three hypervariable regions, also called complementarity-determining regions or CDRs. The extent of the framework region and CDRs have been defined (see, SEQUENCES OF PROTEINS OF IMMUNOLOGICAL INTEREST, Kabat, E., et al., U.S. Department of Health and Human Services, (1987); which is incorporated herein by reference). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable heavy chain to the variable light chain.

The term "contacting" includes reference to placement in direct physical association. With regards to this invention, the term refers to antibody-antigen binding.

As used herein, the term "anti-mesothelin" in reference to an antibody, includes reference to an antibody which is generated against mesothelin. In preferred embodiments, the mesothelin is a primate mesothelin such as human mesothelin. In a particularly preferred embodiment, the antibody is generated against human mesothelin synthesized by a non-primate mammal after introduction into the animal of cDNA which encodes human mesothelin.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table 1:

TABLE 1

Amino Acid Nomenclature

| Name | 3-letter | 1-letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity.

Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table 2 each contain amino acids that are conservative substitutions for one another:

TABLE 2

| | |
| --- | --- |
| 1) | Alanine (A), Serine (S), Threonine (T); |
| 2) | Aspartic acid (D), Glutamic acid (E); |
| 3) | Asparagine (I), Glutamine (Q); |
| 4) | Arginine (R), Lysine (K); |
| 5) | Isoleucine (I), Leucine (L), Methionine (M), Valine (V); and |
| 6) | Phenylalanine (F), Tyrosine (Y), Tryptophan (W). |

See also, Creighton, PROTEINS, W. H. Freeman and Company (1984).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under expressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage displays the foreign protein encoded by the cDNA on its surface. After replication in a bacterial host, typically *E. coli*, the phage which contain the foreign cDNA of interest are selected by the expression of the foreign protein on the phage surface.

"Sequence identity" in the context of two nucleic acid or polypeptide sequences includes reference to the nucleotides (or residues) in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers & Miller, *Computer Applic. Biol. Sci.* 4:11-17 (1988), e.g., as implemented in the program PC/GENE (Intelligenetics, Mountain View, Calif., USA). An indication that two peptide sequences are substantially similar is that one peptide is immunologically reactive with antibodies raised against the second peptide. Thus, a peptide is substantially similar to a second peptide, for example, where the two peptides differ only by a conservative substitution.

A "comparison window", as used herein, includes reference to a segment of about 10-20 residues in which a sequence may be compared to a reference sequence of the same number of contiguous positions after the two sequences are optimally aligned. Methods of alignment of sequences for comparison are well known in the art. Optimal alignment of sequences for comparison may be conducted by the local homology algorithm of Smith & Waterman, *Adv. Appl. Math.* 2:482 (1981); by the homology alignment algorithm of Needleman & Wunsch, *J. Mol. Biol.* 48:443 (1970); by the search for similarity method of Pearson & Lipman, *Proc. Nat'l Acad. Sci. USA* 85:2444 (1988); by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), Madison, Wis., USA); the CLUSTAL program is well described by Higgins & Sharp, *Gene* 73:237-244 (1988) and Higgins & Sharp, *CABIOS* 5:151-153 (1989); Corpet, et al., *Nucl. Acids Res.* 16:10881-90 (1988); Huang, et al., *Computer Applications in the Biosciences* 8:155-65 (1992); and Pearson, et al., *Meth. in Molec. Biol.* 24:307-31 (1994).

The terms "effective amount" or "amount effective to" or "therapeutically effective amount" include reference to a dosage of a therapeutic agent sufficient to produce a desired result, such as inhibiting cell protein synthesis by at least 50%, or killing the cell.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient.

The term "immunoconjugate" includes reference to a covalent linkage of an effector molecule to an antibody. The effector molecule can be an immunotoxin.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE and the B chain of DT) and replacing it with a different targeting moiety, such as an antibody.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

III. Anti-Mesothelin Antibodies

The present invention provides for antibodies targeted to mesothelin. Mesothelin, or CAKI, is a protein present on cells of mesothelial origin, including, but not limited to, ovarian, stomach, squamous cell cancers and mesotheliomas. The immunoconjugates disclosed below target mesothelin using antibodies of the present invention. These antibodies are selectively reactive under immunological conditions to those determinants of mesothelin displayed on the surface of mammalian cells and are accessible to the antibody from the extracellular milieu.

The term "selectively reactive" includes reference to the preferential association of an antibody, in whole or part, with a cell or tissue bearing mesothelin and not to cells or tissues lacking mesothelin. It is, of course, recognized that a certain degree of non-specific interaction may occur between a molecule and a non-target cell or tissue. Nevertheless, selective reactivity, may be distinguished as mediated through specific recognition of mesothelin. Although selectively reactive antibodies bind antigen, they may do so with low affinity. On the other hand, specific binding results in a much stronger association between the antibody and cells bearing mesothelin than between the bound antibody and cells lacking mesothelin or low affinity antibody-antigen binding. Specific binding typically results in greater than 2-fold, preferably greater than 5-fold, more preferably greater than 10-fold and most preferably greater than 100-fold increase in amount of bound antibody (per unit time) to a cell or tissue bearing mesothelin as compared to a cell or tissue lacking mesothelin. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The anti-mesothelin antibodies employed in the present invention can be linked to effector molecules (EM) through the EM carboxyl terminus, the EM amino terminus, through an interior amino acid residue of the EM such as cysteine, or any combination thereof. Similarly, the EM can be linked directly to the heavy, light, Fc (constant region) or framework regions of the antibody. Linkage can occur through the antibody's amino or carboxyl termini, or through an interior amino acid residue. Further, multiple EM molecules (e.g., any one of from 2-10) can be linked to the anti-mesothelin antibody and/or multiple antibodies (e.g., any one of from 2-5) can be linked to an EM. The antibodies used in a multivalent immunoconjugate composition of the present invention can be directed to the same or different mesothelin epitopes.

In preferred embodiments of the present invention, the anti-mesothelin antibody is a recombinant antibody such as a scFv or disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In a particularly preferred embodiment, the antibody is a single chain Fv (scFv). The $V_H$ and the $V_L$ regions of a scFv antibody comprise a single chain which is folded to create an antigen binding site similar to that found in two-chain antibodies. Once folded, noncovalent interactions stabilize the single chain antibody. In a more preferred embodiment, the scFv is recombinantly produced. In yet another preferred embodiment, the $V_H$ region has the amino acid sequence as shown in FIG. 1. In the most preferred embodiment, the $V_H$ region has the nucleic acid sequence as found in SEQ ID NO:1. In another preferred embodiment, the $V_L$ region has the amino acid sequence as found in FIG. 1. In a more preferred embodiment, the $V_L$ region has the nucleic acid sequence as indicated in SEQ ID NO:1. In yet a further embodiment, the CDRs have the amino acid sequences as shown in FIG. 1. In a more preferred embodiment, the CDRs have the nucleic acid sequence as shown in SEQ ID NO:1. In the most preferred embodiment, the entire scFv has the nucleic acid sequence shown in SEQ ID NO:1. One of skill will realize that conservative variants of the antibodies of the instant invention can be made. Such conservative variants employed in scFv fragments will retain critical amino acid residues necessary for correct folding and stabilizing between the $V_H$ and the $V_L$ regions. Conservatively modified variants of the prototype sequence of SEQ ID NO:1 have at least 80% sequence similarity, preferably at least 85% sequence similarity, more preferably at least 90% sequence similarity, and most preferably at least 95% sequence similarity at the amino acid level to its prototype sequence.

In some embodiments of the present invention, the scFv antibody is directly linked to the EM through the light chain. However, scFv antibodies can be linked to the EM via its amino or carboxyl terminus.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. No. 4,946,778, U.S. Pat. No. 5,132,405 and Stemmer, et al., *Biotechniques* 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Ser (SEQ ID NO:7), preferably 2, 3, 4, 5, or 6 such sequences. However, it is to be appreciated that some amino acid substitutions within the linker can be made. For example, a valine can be substituted for a glycine.

A. Antibody Production

Methods of producing polyclonal antibodies are known to those of skill in the art. In brief, an immunogen, preferably isolated mesothelin or extracellular mesothelin epitopes are mixed with an adjuvant and animals are immunized with the mixture. When appropriately high titers of antibody to the immunogen are obtained, blood is collected from the animal and antisera are prepared. If desired, further fractionation of the antisera to enrich for antibodies reactive to the polypeptide is performed. See, e.g., Coligan, CURRENT PROTOCOLS IN IMMUNOLOGY, Wiley/Greene, NY (1991); and Harlow & Lane, supra, which are incorporated herein by reference.

Monoclonal antibodies may be obtained by various techniques familiar to those skilled in the art. Description of techniques for preparing such monoclonal antibodies may be found in, e.g., Stites, et al. (eds.) BASIC AND CLINICAL IMMUNOLOGY (4TH ED.), Lange Medical Publications, Los Altos, Calif., and references cited therein; Harlow & Lane, supra; Goding, MONOCLONAL ANTIBODIES: PRINCIPLES AND PRACTICE (2D ED.), Academic Press, New York, N.Y. (1986); Kohler & Milstein, *Nature* 256:495-497 (1975); and particularly (Chowdhury, P. S., et al., *Mol. Immunol.* 34:9 (1997)), which discusses one method of generating monoclonal antibodies.

It is preferred here that monoclonal antibodies are made by immunizing an animal with a nucleic acid sequence that encodes the desired immunogen, in this case, mesothelin. Immunization with non-replicating transcription units that encode heterologous protein(s) elicits antigen specific immune responses. After translation into the foreign protein, the protein is processed and presented to the immune system like other cellular proteins. Because it is foreign, an immune response is mounted against the protein and peptide epitopes that are derived from it (Donnelly, et al., *J. Immunol. Methods* 176:145-152 (1994); and Boyer, et al., *J. Med. Primatol.* 25:242-250 (1996)). This technique has two significant advantages over protein-based immunization. One is that it does not require the purification of the protein, which at best, is time consuming and in cases of many membrane proteins, is very difficult. A second advantage is that since the immunogen is synthesized in a mammalian host, it undergoes proper post-translational modifications and folds into the native structure.

To immunize with mesothelin-coding DNA, mesothelin-coding cDNA is introduced into a plasmid so that transcription of the coding sequence is under the control of a promoter such as the CMV promoter. The plasmid is then injected into an animal, either subcutaneously, intradermally, intraperitoneally, etc. As a result, the mesothelin cDNA is transcribed in the animal into mRNA, mesothelin is translated from the mRNA, the translated protein undergoes proper posttranslational modifications and is expressed on the surface of cells which synthesized mesothelin. The animal raises antibodies to mesothelin and the sera is monitored for antibody titer.

Optionally, in addition to the coding region and regulatory elements, the plasmid carries an ampicillin resistance (Amp) gene. The Amp gene is known to have immunostimulatory sequences for Th1 responses necessary for increased antibody production (Sato, et al., *Science* 273:352-354 (1996)).

In a particularly preferred embodiment, mice are immunized intradermally with pcD3CAK1-9 which expresses mesothelin under the control of a CMV promoter (Chang, et al., *Nat'l Acad. Sci. USA* 93:136-140 (1996)). Balb/c mice are particularly preferred because intradermal DNA immunization has been shown to induce strong humoral immune response in this strain (Raz, et al., *Proc. Nat'l Acad. Sci. USA* 93:5141-5145 (1996)).

As described above, in preferred embodiments, the monoclonal antibody is a scFv. Methods of making scFv antibodies have been described. See, Huse, et al., supra; Ward, et al. *Nature* 341:544-546 (1989); and Vaughan, et al., supra. In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., *Mol. Immunol.* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes.

In a particularly preferred embodiment, scFv are chosen through a phage display library. After antibody titers against the antigen in the immunized animal reach their maximum, the animal is sacrificed and the spleen removed. The procedure described above for synthesizing scFv is followed. After amplification by PCR, the scFv nucleic acid sequences are fused in frame with gene III (gIII) which encodes the minor surface protein gIIIp of the filamentous phage (Marks, et al., *J. Biol. Chem.* 267:16007-16010 (1992); Marks, et al., *Behring Inst. Mitt.* 91:6-12 (1992); and Brinkmann, et al., *J. Immunol. Methods* 182:41-50 (1995)). The phage express the resulting fusion protein on their surface. Since the proteins on the surface of the phage are functional, phage bearing mesothelin-binding antibodies can be separated from non-binding or lower affinity phage by panning or antigen affinity chromatography (McCafferty, et al., *Nature* 348:552-554 (1990)).

In a preferred embodiment, scFv that specifically bind to mesothelin are found by panning. Panning is done by coating a solid surface with mesothelin and incubating the phage on the surface for a suitable time under suitable conditions. The unbound phage are washed off the solid surface and the bound phage are eluted. Finding the antibody with the highest affinity is dictated by the efficiency of the selection process and depends on the number of clones that can be screened and the stringency with which it is done. Typically, higher stringency corresponds to more selective panning. However, if the conditions are too stringent, the phage will not bind. After one round of panning, the phage that bind to mesothelin coated plates are expanded in E. coli and subjected to another round of panning. In this way, an enrichment of 2000-fold occurs in 3 rounds of panning. Thus, even when enrichment in each round is low, multiple rounds of panning will lead to the isolation of rare phage and the genetic material contained within which encodes the sequence of the highest affinity antibody. The physical link between genotype and phenotype provided by phage display makes it possible to test every member of a cDNA library for binding to antigen, even with libraries as large as 100,000,000 clones.

B. Binding Affinity of Antibodies

The antibodies of this invention specifically bind to an extracellular epitope of mesothelin. An anti-mesothelin antibody has binding affinity for mesothelin if the antibody binds or is capable of binding mesothelin as measured or determined by standard antibody-antigen assays, for example, competitive assays, saturation assays, or standard immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($k_D=1/K$, where K is the affinity constant) of the antibody is <1 µM, preferably <100 nM, and most preferably <0.1 nM. Antibody molecules will typically have a $k_D$ in the lower ranges. $k_D=[Ab-Ag]/[Ab][Ag]$ where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds. This method of defining binding specificity applies to single heavy and/or light chains, CDRs, fusion proteins or fragments of heavy and/or light chains, that are specific for mesothelin if they bind mesothelin alone or in combination.

C. Immunoassays

The antibodies can be detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (e.g., mesothelin) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the antimesothelin antibody. Alternatively, the labeling agent may be a third moiety, such as another antibody, that specifically binds to the antibody/mesothelin protein complex.

In one aspect, a competitive assay is contemplated wherein the labeling agent is a second anti-mesothelin antibody bearing a label. The two antibodies then compete for binding to the immobilized mesothelin. Alternatively, in a non-competitive format, the mesothelin antibody lacks a label, but a second antibody specific to antibodies of the species from which the anti-mesothelin antibody is derived, e.g., murine, and which binds the antimesothelin antibody, is labeled.

Other proteins capable of specifically binding immunoglobulin constant regions, such as Protein A or Protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., J. Immunol. 111: 1401-1406 (1973); and Akerstrom, et al., J. Immunol. 135: 2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting anti-mesothelin antibodies in a sample containing the antibodies generally comprises the steps of contacting the sample with an antibody which specifically reacts, under immunologically reactive conditions, to the mesothelin/antibody complex.

IV. Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified Pseudomonas exotoxin or Diphtheria toxin, encapsulating agents, (e.g., liposomes) which themselves contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native EM or anti-mesothelin antibodies can be modified to form the EM, antibodies, or immunoconjugates of the present invention. Modification by site-directed mutagenesis is well known in the art. Nucleic acids encoding EM or anti-mesothelin antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well-known to persons of skill.

In a preferred embodiment, immunoconjugates are prepared by inserting the cDNA which encodes an anti-mesothelin scFv antibody into a vector which comprises the cDNA encoding the EM. The insertion is made so that the scFv and the EM are read in frame, that is in one continuous polypeptide which contains a functional Fv region and a functional EM region. In a particularly preferred embodiment, cDNA encoding a diphtheria toxin fragment is ligated to a scFv so that the toxin is located at the carboxyl terminus of the scFv. In a most preferred embodiment, cDNA encoding PE is ligated to a scFv so that the toxin is located at the amino terminus of the scFv.

Once the nucleic acids encoding an EM, anti-mesothelin antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-mesothelin antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

In addition to recombinant methods, the immunoconjugates, EM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer—Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially described by Buchner, et al., supra.

Renaturation is typically accomplished by dilution (e.g, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

V. *Pseudomonas* Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diptheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 $k_D$ respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060, 165).

Abrin includes toxic lectins from *Abrus precatorius*. The toxic principles, abrin a, b, c, and d, have a molecular weight of from about 63 and 67 $k_D$ and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin (PE). The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:8) and REDL (SEQ ID NO:9). See Siegall, et al., *J. Biol. Chem.* 264:14256 (1989). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided as SEQ ID NO:1 of commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., *J. Biol. Chem.* 264: 14256-14261 (1989), incorporated by reference herein.

PE employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, and PE35. PE40 is a truncated derivative of PE as previously described in the art. See, Pai, et al., *Proc. Nat'l Acad. Sci. USA* 88:3358-62 (1991); and Kondo, et al., *J. Biol. Chem.* 263:9470-9475 (1988). PE35 is a 35 $K_D$ carboxyl-terminal fragment of PE composed of a met at position 280 followed by amino acids 281-364 and 381-613 of native PE. In preferred embodiments, the cytotoxic fragment PE38 is employed. PE38 is a truncated PE pro-protein composed of amino acids 253-364 and 381-613 which is activated to its cytotoxic form upon processing within a cell (see U.S. Pat. No. 5,608,039, incorporated herein by reference).

In a particularly preferred embodiment, PE38 is the toxic moiety of the immunotoxin of this invention, however, other cytotoxic fragments PE35 and PE40 are contemplated and are disclosed in U.S. Pat. Nos. 5,602,095 and 4,892,827, each of which is incorporated herein by reference.

A. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity of PE

*Pseudomonas* exotoxins employed in the invention can be assayed for the desired level of cytotoxicity by assays well known to those of skill in the art. Exemplary toxicity assays are described herein at, e.g., Example 2. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

C. Other Therapeutic Moieties

Antibodies of the present invention can also be used to target any number of different diagnostic or therapeutic compounds to cells expressing mesothelin on their surface. Thus, an antibody of the present invention, such as an anti-mesothelin scFv, may be attached directly or via a linker to a drug that is to be delivered directly to cells bearing mesothelin. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-mesothelin antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., *Pharm. Ther.* 28:341-365 (1985).

D. Detectable Labels

Antibodies of the present invention may optionally be covalently or noncovalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

E. Conjugation to the Antibody

In a non-recombinant embodiment of the invention, effector molecules, e.g., therapeutic, diagnostic, or detection moieties, are linked to the anti-mesothelin antibodies of the present invention using any number of means known to those of skill in the art. Both covalent and noncovalent attachment means may be used with anti-mesothelin antibodies of the present invention.

The procedure for attaching an effector molecule to an antibody will vary according to the chemical structure of the EM. Polypeptides typically contain variety of functional groups; e.g., carboxylic acid (COOH), free amine ($-NH_2$) or sulfhydryl ($-SH$) groups, which are available for reaction with a suitable functional group on an antibody to result in the binding of the effector molecule.

Alternatively, the antibody is derivatized to expose or attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

VI. Pharmaceutical Compositions and Administration

The antibody and/or immunoconjugate compositions of this invention (i.e., PE linked to an anti-mesothelin antibody), are particularly useful for parenteral administration, such as intravenous administration or administration into a body cavity or lumen of an organ. For example, ovarian malignancies may be treated by intravenous administration or by localized delivery to the tissue surrounding the tumor. To treat mesotheliomas, the pharmaceutical compositions of this invention can be administered directly into the pleural or peritoneal cavities.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339 (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et at., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is the treatment of malignant cells expressing mesothelin. Exemplary malignant cells include ovarian, stomach and squamous cell cancers as well as mesotheliomas.

VII. Diagnostic Kits

In another embodiment, this invention provides for kits for the detection of mesothelin or an immunoreactive fragment thereof, (i.e., collectively, a "mesothelin protein") in a biological sample. A "biological sample" as used herein is a sample of biological tissue or fluid that contains mesothelin. Such samples include, but are not limited to, tissue from biopsy, sputum, amniotic fluid, blood, and blood cells (e.g., white cells). Fluid samples may be of some interest, but are generally not preferred herein since detectable concentrations of mesothelin are rarely found in such a sample. Biological samples also include sections of tissues, such as frozen sections taken for histological purposes. A biological sample is typically obtained from a multicellular eukaryote, preferably a mammal such as rat, mice, cow, dog, guinea pig, or rabbit, and most preferably a primate such as macaques, chimpanzees, or humans.

Kits will typically comprise an anti-mesothelin antibody of the present invention. In some embodiments, the anti-mesothelin antibody will be an anti-mesothelin Fv fragment; preferably a scFv fragment.

In addition the kits will typically include instructional materials disclosing means of use of an antibody of the present invention (e.g. for detection of mesothelial cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting mesothelin in a biological sample generally comprises the steps of contacting the biological sample with an antibody which specifically reacts, under immunologically reactive conditions, to mesothelin. The antibody is allowed to bind to mesothelin under immunologically reactive conditions, and the presence of the bound antibody is detected directly or indirectly.

Although the present invention has been described in some detail by way of illustration and example for purposes of clarity of understanding, it will be obvious that certain changes and modifications may be practiced within the scope of the appended claims.

VIII. EXAMPLES

Example 1

Synthesis of 55. scFv Antibodies

Immunization of Mice

Four month old female Balb/c mice were immunized intradermally with 15 μg of the plasmid, pcD3CAK1-9, which contains the coding sequence for full length mesothelin (Chang, et al., *Nat'l Acad. Sci. USA* 93:136-140 (1996)) in 0.15 M NaCl. After 3 weeks, four booster intradermal injections of 15 μg pcD3CAK1-9 were given at intervals of three to five weeks. The spacing between the injections was determined by following the anti-mesothelin antibody titer in the blood by ELISA. The titer was defined as the reciprocal of the highest dilution of anti-serum which gave an ELISA signal 2-3-fold higher than the background. Each booster injection was given when the titer in the blood declined from a peak level except for the last injection which was given when the titer remained at a plateau for five weeks. Ten days after the last injection, the antibody titer was more than 100,000 as measured by ELISA using recombinant mesothelin. At this time, the mice were sacrificed and the spleens collected.

RNA Extraction and Initial Construction of the scFv Library

These procedures were performed as described earlier (Chowdhury, et al., *Mol. Immunol.* 34:9-20 (1997)) with the following modifications. About 150 ng of scFv DNA insert was used for ligation into 125 ng of SfiI and NotI cut pCANTAB5E and the library was made in XL-1 blue MRF' cells instead of XL-2 blue MRF'. The library contained about $9 \times 10^5$ independent clones. Glucose was added to the library, which was in 18 mL SOC medium, to a final concentration of 2% (w/v). After incubation at 37° C. for 90 min, ampicillin and tetracycline were added to final concentrations of 100 and 10 μg/mL, respectively. Incubation was continued at 37° C. for another 90 min and the cultures stored as glycerol stocks.

Characterization of the Selected Clone

Figure 2:
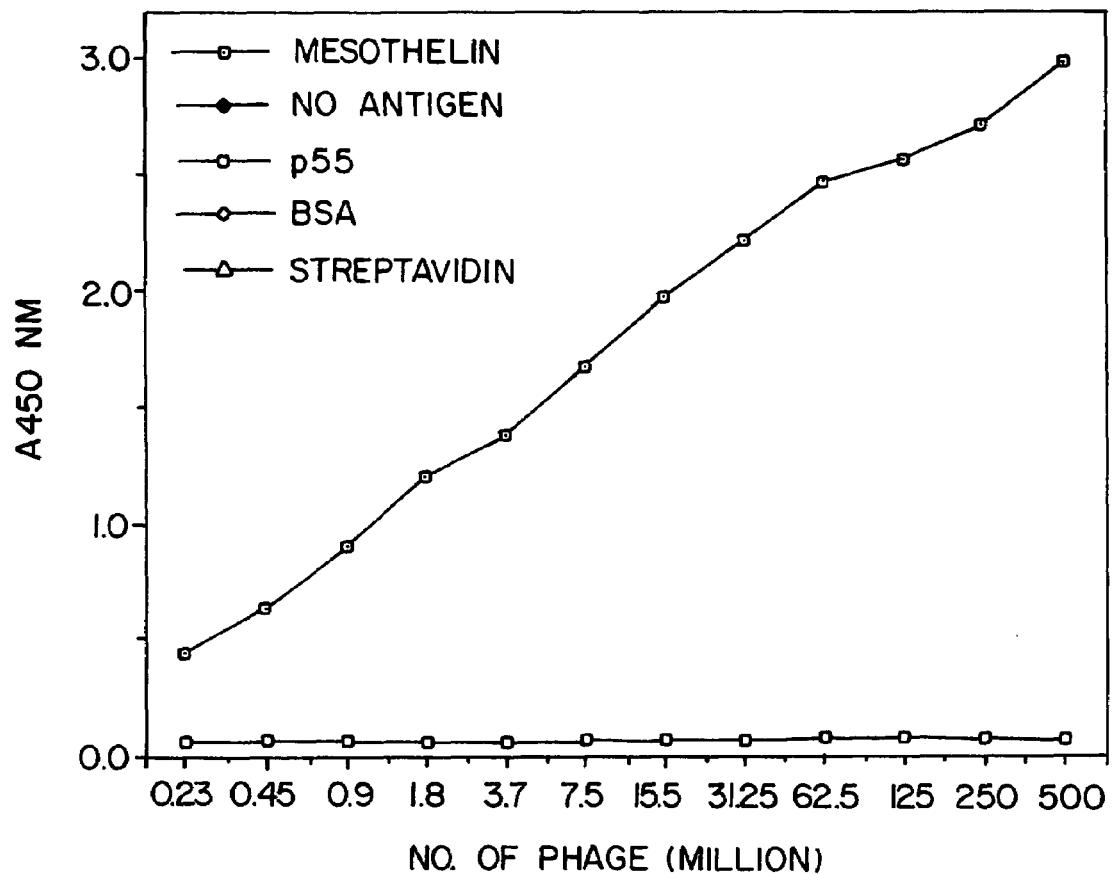
FIG. 2.
Figure 3:
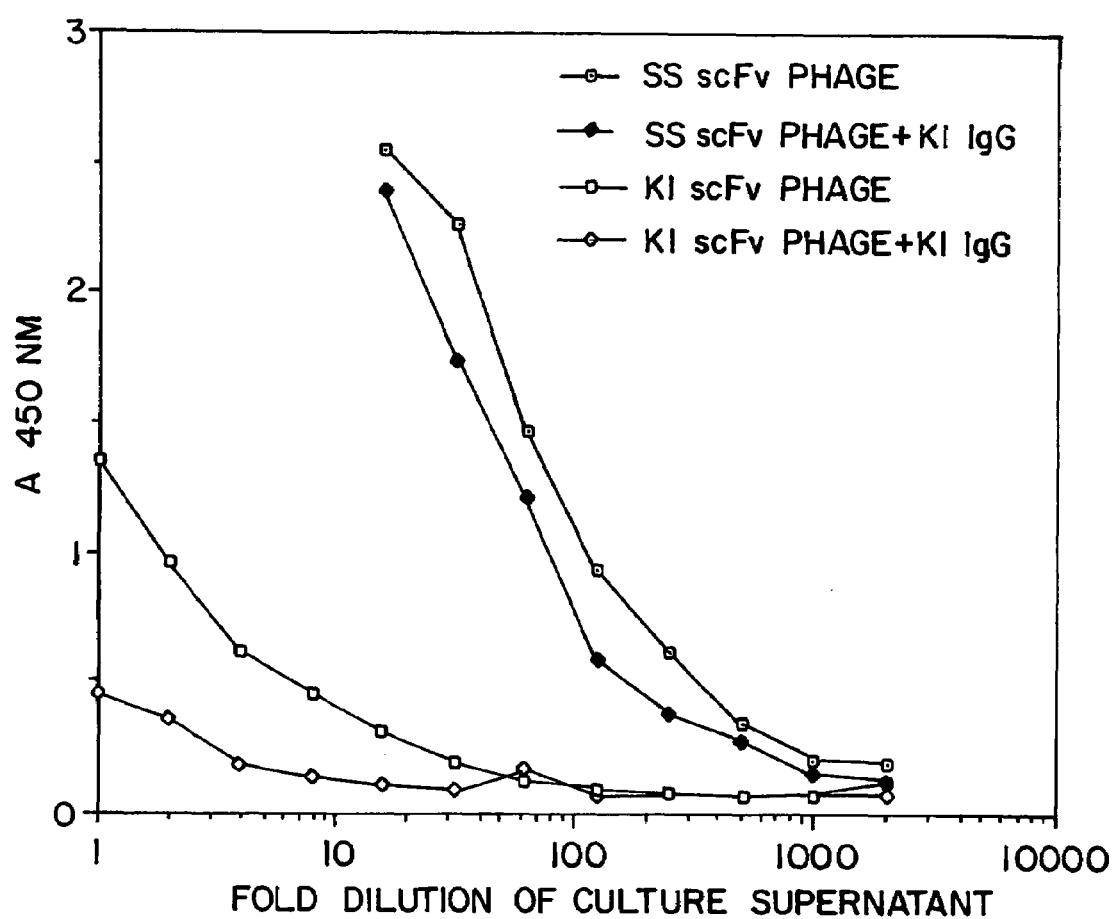
FIG. 3.

Recombinant phage were rescued by superinfection with the helper phage M13KO7 and tested for binding to recombinant mesothelin (a.a. 291-606). FIG. 2 demonstrates the phage bound to mesothelin in a concentration-dependent manner and did not show any binding to ELISA wells that were uncoated or were coated with various control proteins. This indicated that the phage displaying an anti-mesothelin scFv antibody (SS scFv) was specific for mesothelin. To determine if the SS scFv phage bound to a different epitope of mesothelin than MAb K1 (see Chang, et al., *Int'l J. Cancer* 57:90 (1994)), a competition ELISA was performed. As a positive control, inhibition of binding of a K1 phage by isolated and purified K1 IgG was tested in parallel. As shown in FIG. 3, the binding of the SS scFv phage was only slightly inhibited by K1 IgG and there was no concentration dependence of the inhibition, whereas binding of the K1 phage was greatly reduced by K1 IgG. This indicated that the epitope to which SS scFv is directed was different from that of K1.

Transfer of the Library from *E. coli* XL-1 to the TG1 Strain

During the panning and reamplification process in XL-1 (see infra), frequent deletion of the scFv sequences from the phagemid were noticed. The library was therefore transferred to the TG-1 strain for panning. First, polyethylene glycol (PEG)-precipitated recombinant phage were rescued from a pool of glycerol stocks of the library in XL-1. TG1 cells (50 mL) at an ODD$_{600nm}$ of 0.55 in 2XYT were infected with the rescued phage at a multiplicity of infection (m.o.i.) of five. Incubation was at 37° C. for 30 min with shaking at 110 rpm and then for 30 min at 250 rpm. Ampicillin (100 µg/mL) was added and the culture was further incubated for 30 min at 37° C. at 250 rpm. Recombinant phagemid particles were rescued with M13KO7 as described (Chowdhury, et al., *Mol. Immunol.* 34:9-20 (1997)) except that rescue was at 37° C. and 30° C. in separate cultures. The phage were PEG-precipitated three times (Lin, et al., *J. Biol. Chem.* 255:10331-10337 (1980)) before being used for panning on recombinant mesothelin (a.a. 291-606).

Panning of the Library

Recombinant mesothelin was prepared as described in Chowdhury, et al., *Mol. Immunol.* 34:9-20 (1997). Panning was done at 37° C. to select for a scFv that would be stable at this temperature.

Method 1 (direct panning): 35 mm diameter wells of tissue culture grade plates were coated with 1.5 mL of recombinant mesothelin at 5 µg/mL (125 nM) in 50 mM bicarbonate buffer pH 9.4, and blocked with 3% non-fat milk in PBS containing 0.05% Tween 20 (TPBS). In the first round of panning, 2×10$^{11}$ colony forming units were added. After 2 hours at 37° C. and after 20 rounds of washing with TPBS and PBS, 7×10$^4$ phage remained on the plate. The bound phage were eluted with 1 mL of 50 mM HCl, pH 1.3, for 10 minutes at 37° C. After neutralization with Tris buffer, an aliquot of the eluate was used for titration on LB plates containing 100 µg/mL ampicillin and 2% glucose. The rest was used to infect 10 mL *E. coli* TG1 cells grown to a OD$_{600}$ of 0.3 in 2XYT. During this infection phase, glucose was added to the culture for a final concentration of 2%. The culture was incubated at 37° C. for 30 min with shaking at 110 rpm and then for 30 min at 250 rpm. Ampicillin was added to a final concentration of 100 µg/mL and the culture incubated for an additional 30 min at 37° C. with shaking at 250 rpm and followed by the addition of M13KO7 at a m.o.i. of 15. The culture was incubated for 60 min at 37° C. with shaking at 110 rpm for the first 30 min and then at 250 rpm. The cells were pelleted and resuspended in 20 mL 2×YT medium containing 100 µg/mL ampicillin and 50 µg/mL kanamycin. The culture was incubated at 37° C. with shaking at 250 rpm overnight. The rescued phage in the culture medium were PEG-precipitated, titrated and used for the next round of panning. After the third round of panning, ten clones were selected randomly and DNA minipreps were analyzed for BstN1 fingerprinting and nucleotide sequence analysis.

Method 2 (off-rate panning): The procedure described above was followed except that after washing the unbound phage particles the plates were incubated at 37° C. in PBS for an additional 2 hrs. before eluting the bound phage to select for phage which would have a slower off rate.

Results

Titration of eluted phage from both direct and off-rate panning showed that there was a 1000-2000 fold enrichment in the number of eluted phage between the first and third round of panning (Table 1).

TABLE 1

Enrichment of Anti-mesothelin Phage Over Three Rounds of Panning at 37° C. Using Direct or Off-rate Selection

| Panning round (Selection) | Input no. of phage | No. of phage binding | No. of mesothelin positive phage/No. tested |
|---|---|---|---|
| 1 Direct | 2 × 10$^{11}$ | 7 × 10$^4$ | 0/48 |
| Off-rate | 2 × 10$^{11}$ | 2 × 10$^4$ | 0/48 |
| 2 Direct | 7 × 10$^{10}$ | 8 × 10$^4$ | 2/48 |
| Off-rate | 3 × 10$^{10}$ | 8 × 10$^3$ | 1/48 |
| 3 Direct | 1 × 10$^{10}$ | 6 × 10$^6$ | 32/48 |
| Off-rate | 3 × 10$^9$ | 4 × 10$^5$ | 30/48 |

After each round of panning, recombinant phage were rescued from 48 randomly picked individual phagemid colonies. Initially, there was no detectable mesothelin positive clone among colonies picked randomly from the unpanned library. Also there was none in the eluate after the first round of panning (see Table 1). In the eluate after the second round of panning, there were 1-2 mesothelin positive clones out of 48 tested. In the third eluate the number increased to about 30/48. BstN1 fingerprinting of six positive clones from each group showed that the restriction pattern was identical for all the clones. DNA sequencing of six clones from each group after three rounds of panning revealed that the positive clones obtained were identical in their nucleotide sequence.

A similar selection process was carried out using phage grown and selected at 30° C. and the same clone was obtained. The single scFv clone capable of binding to mesothelin was termed SS scFv. The amino acid sequence obtained from a translation of the nucleotide sequence of SS scFv is shown in FIG. 1. The nucleotide sequence has been deposited in the GenBank database as Accession Number AF035617. According to Kabat's classification, the V$_H$ belongs to sub-group IIA and family V and the V$_L$ belongs to sub-group VI and family XI.

Example 2

Analysis of SI scFv

SS scFv was analyzed to determine whether it would be a candidate as the targeting moiety of an immunotoxin. Previously, it was found that murine monoclonal antibodies raised against recombinant mesothelin (isolated from bacteria inclusion bodies) bound recombinant mesothelin but did not bind native, mammalian cell-derived mesothelin with high affinity. A phage display library was made from the splenic mRNA of the immunized mice and scFvs which bound to recombinant mesothelin were found. However, immunotoxins prepared from these antibodies did not kill cells which express mesothelin. It was hypothesized that these antibodies had low affinity for human mesothelin as found on cell surfaces. In addition, another murine antibody against mesothelin, K1, was coupled to PE40. This immunotoxin too failed to kill mesothelin-expressing cells (Chang, et al., *Cancer Res.* 52:181 (1992)).

Binding Assays

Binding of phage to mesothelin was assayed by enzyme linked immunosorbent assay (ELISA). (A) Wells of IMMUNOLON-4® plates were coated with 200 ng mesothelin (a.a. 291-606), BSA, the p55 subunit of the IL-2 receptor or streptavidin in 100 µL bicarbonate buffer, pH 9.4, overnight at 4° C. The wells were blocked with 3% non-fat dry milk in TPBS for 60 min. 100 µL of blocking solution containing varying numbers of phage was applied to each well and incubated for 60 min at 37° C. After washing with TPBS, bound phage were detected with an anti-M13 antibody conjugated to HRP for 60 min at 37° C. After washing with TPBS and PBS, the ELISA wells were developed with 100 µL BM-Blue substrate (Boehringer-Mannheim) for HRP. Color development was stopped after 2 minutes with 100 µL 2 N $H_2SO_4$ and the O.D. readings were taken at 450 nm.

(B) Competition ELISA—Competition ELISA was performed on immobilized recombinant mesothelin as described above except that 100 µL of various dilutions of TG1 culture supernatant SS scFv or K1 scFv recombinant phagemid particles was used directly for ELISA either with or without 1.0 µg K1 IgG.

Immunofluorescence Examination of Live Cells

To determine if the antibody selected by panning on recombinant mesothelin (a.a. 291-606) bound to mesothelin displayed on a mammalian cell surface, an immunofluorescence assay was performed with mesothelin-positive cells. NIH 3T3 is a Swiss mouse fibroblast cell line. NIH 3T3K20 is stably transfected with a eukaryotic expression vector (pcDNA3) containing the full length mesothelin gene (pcD3CAK1-9). A431 is a cervical epidermoid carcinoma and A431-K5 is stably transfected with pcD3CAK1-9. Other cell lines were previously described (Chang, et al., *Cancer Res.* 52:181-186 (1992); and Reiter, et al., *Biochemistry* 33:5451-5459 (1994)).

The cells were grown in 35 mm tissue culture dishes. The cells were washed with DPBS containing $Ca^{2+}$ and $Mg^{2+}$ (DPBS++) and cooled over ice. The cells were blocked with 0.2% BSA in DPBS++ at 4° C. and exposed to $10^{11}$ phage particles selected by panning or to anti-Tac phage, which displays a scFv to p55 subunit of the IL-2 receptor, for 60 minutes at 4° C. Bound phage were detected with a mouse MAb to gVIIIp of M13 phage as the first antibody followed by goat anti mouse IgG coupled to rhodamine as the detecting antibody. After washing, the cells were fixed in 3.7% formaldehyde and mounted in situ under cover slips in buffered glycerol.

Figure 4:
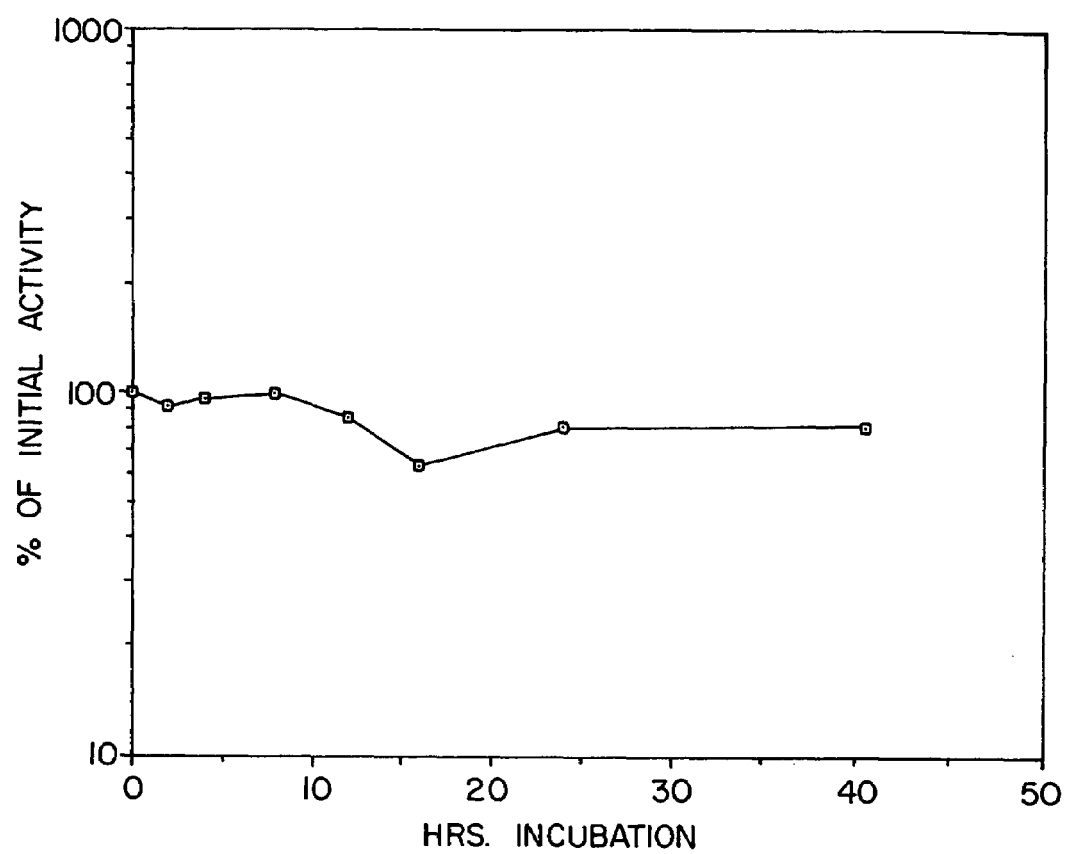
FIG. 4.

FIG. 4 shows that phage which display SS scFv did not bind to mesothelin-negative NIH 3T3 cells but did bind strongly to NIH 3T3 K20 cells. A control phage which displayed anti-Tac scFv did not bind to either of these cell lines. These results indicated that SS scFv specifically bound to cell surface mesothelin.

Example 3

Synthesis at *Pseudomonas aeruginosa* Exotoxin

Construction of a Plasmid for Expression and Purification of Immunotoxin SS(scFv) PE38

To determine if the SS scFv could target a cytotoxic agent to mesothelin positive cells, a recombinant immunotoxin was constructed by fusing SS scFv to PE38, a truncated form of *Pseudomonas* exotoxin A. In this construction, the SS scFv replaced the binding domain of PE and targeted the toxin to cells to which SS scFv bound, i.e., mesothelin-expressing cells.

The scFv from the phagemid vector pPSC7-1 was PCR amplified using primer pairs New G2 Nde1 5'-TAAGAAG-GAGATATACATATGCAGGTACAACTG-CAGCAGTCTGGG-3' (SEQ ID NO:3) as the back primer and New G2 HindIII 5'-GCCCTCGGGACC TCCG-GAAGCTTTTATTTCCAACTTTGTCCC-3' (SEQ ID NO:4) as the forward primer. These primers introduced a Nde1 and a HindIII site at the 5' and 3' ends of SS scFv. After agarose gel purification, the PCR product was digested with Nde1 and HindIII and ligated into the 4180 bp fragment of pUL17 (Benhar, et al., *Bioconjugate Chem.* 5:321-326 (1994)) obtained by cutting with the same enzymes. The resulting plasmid, pPSC7-2, had SS scFv fused in frame with domain II and III of *Pseudomonas* exotoxin A (SEQ ID NO:2). Competent *E. coli* were transformed and recombinant proteins were found in inclusion bodies (Brinkmann, et al., *Proc. Nat'l Acad. Sci. USA* 88:8616-8620 (1991)).

After renaturation from inclusion bodies, the SS scFv-PE38 was purified by ion exchange and size exclusion chromatography. The recombinant immunotoxin eluted as a monomer from a TSK gel filtration column and migrated as a single band of about 67 kD by SDS-PAGE. Calculating from total inclusion body proteins subjected to refolding, the yield of protein was about 12%.

Example 4

In Vitro, Activity of SS scFv-PE38

Binding Assays

The binding characteristics of the immunotoxin was determined by surface plasmon resonance (Brinkmann, et al., *Int. J. Cancer* 71:638-644 (1997)). Recombinant mesothelin (a.a. 291-606) was coupled to BIACore sensor chip CM5 and a 25 µg/mL solution of the immunotoxin was run over the chip. The $k_{on}$ was found to be $1.68 \times 10^5$ $M^{-1}$ $sec^{-1}$. The $k_{off}$ was found to be $1.83 \times 10^3$ $sec^{-1}$. The dissociation constant or $K_d$ calculated from these data was 11 nM.

Cytotoxicity Assays

The ability of the SS scFv-PE38 to inhibit protein synthesis was used as a measure of its cytotoxic effect (Chaudhary, et al., *Nature* 339:394-397 (1989)). To determine if SS scFv could be internalized so that the toxin could kill the target cells, mesothelin-positive and mesothelin-negative cells were exposed to the immunotoxin for 20 hours in the presence of $^3$H-leucine and $^3$H incorporation was determined. On A431-K5 cells, which express mesothelin, the amount of immunotoxin required to inhibit protein synthesis by 50% or $IC_{50}$ was found to be 0.5 ng/mL (Table 2), whereas on ATAC4 cells, which express the p55 subunit of the IL-2 receptor, the $IC_{50}$ was 400 ng. On nontransfected A431 cells, the $IC_{50}$ was found to be 450 ng/mL. Thus, the cytotoxic activity of SS scFv-PE38 was found to be highly specific.

TABLE 2

Cytotoxicity of SS scFv-PE38 on human cancer cell lines

| Cell line | Origin | [Ki or SS] reactivity by IF | $IC_{50}$ ng/mL |
|---|---|---|---|
| A431 | Epidermoid carcinoma | — | 450 |
| A431 K5 | Mesothelin transfected A431 | ++++ | 0.5 |
| ATAC-4 | p55 transfected A431 | — | 400 |
| AGS | Gastric adenocarcinoma | ++ | 6 |
| N87 | Gastric adenocarcinoma | ++ | 6 |
| A1847 | Ovarian adenocarcinoma | ++/het | 16 |
| JD38 | Burkitt's lymphoma | — | >1000 |
| Raji | Burkitt's lymphoma | — | >1000 |
| HUT 102 | T-cell leukemia | — | >1000 |

The recombinant immunotoxin was also tested with several antigen negative cell lines (HUT102, Raji, and JD38) and showed very little cytotoxic activity ($IC_{50}$>1,000 ng/mL). However, with the mesothelin positive ovarian cancer cell line A1847, the $IC_{50}$ was found to be 16 ng/mL. Two gastric carcinoma cell lines, AGS and N87, which express mesothelin were sensitive to SS scFv-PE38 with an $IC_{50}$ of 6 ng/mL. These studies indicated that sufficient amounts of SS scFv-PE38 were internalized to kill mesothelin-positive cell lines.

Stability Assays

To be useful in targeted therapy, a scFv must be stable for many hours at 37° C. while it penetrates the interior of tumors (Brinkmann, et al., *Biochem. Biophys. Acta* 1198: 27-45 (1994)). The stability of the SS scFv-PE38 immunotoxin was analyzed by measuring the cytotoxic activity of aliquots of a 10 μg/mL stock in 0.2% human serum albumin (HSA) in DPBS++after incubation at 37° C. for varying periods of time. At the end of the incubation, the samples were stored at −80° C. and tested for their cytotoxic activity on A431-K5 cells.

FIG. 4 shows that following incubation at 37° C. for up to 40.5 hours, there was barely any change in the cytotoxic activity of the immunotoxin, indicating that the molecule was very stable at physiological temperature.

Example 5

In vivo Antitumor Activity of SS scFv-PE38

SS scFv-PE38 was assayed for its ability to inhibit the growth or cause regression of subcutaneous tumor xenografts in nude mice. This was done by injecting $1.5 \times 10^6$ A431-K5 cells subcutaneously into 4-6 week old nude mice on day 0. Treatment was started on day 4 when tumors measured about 50 $mm^3$. Animals were treated intravenously with three doses of 2.6 or 4.3 μg of SS scFv-PE38 on days 5, 7 and 9. The control group received either anti-Tac (scFv)-PE38, which had been previously shown to produce complete regression of tumors expressing the IL-2 receptor (Reiter, Y., et al., *Int. J. Cancer* 58:142 (1994)) but which is not cytotoxic to A431-K5 cells, or the carrier (0.2% HSA in DPBS). Each group consisted of five animals.

Figure 5:
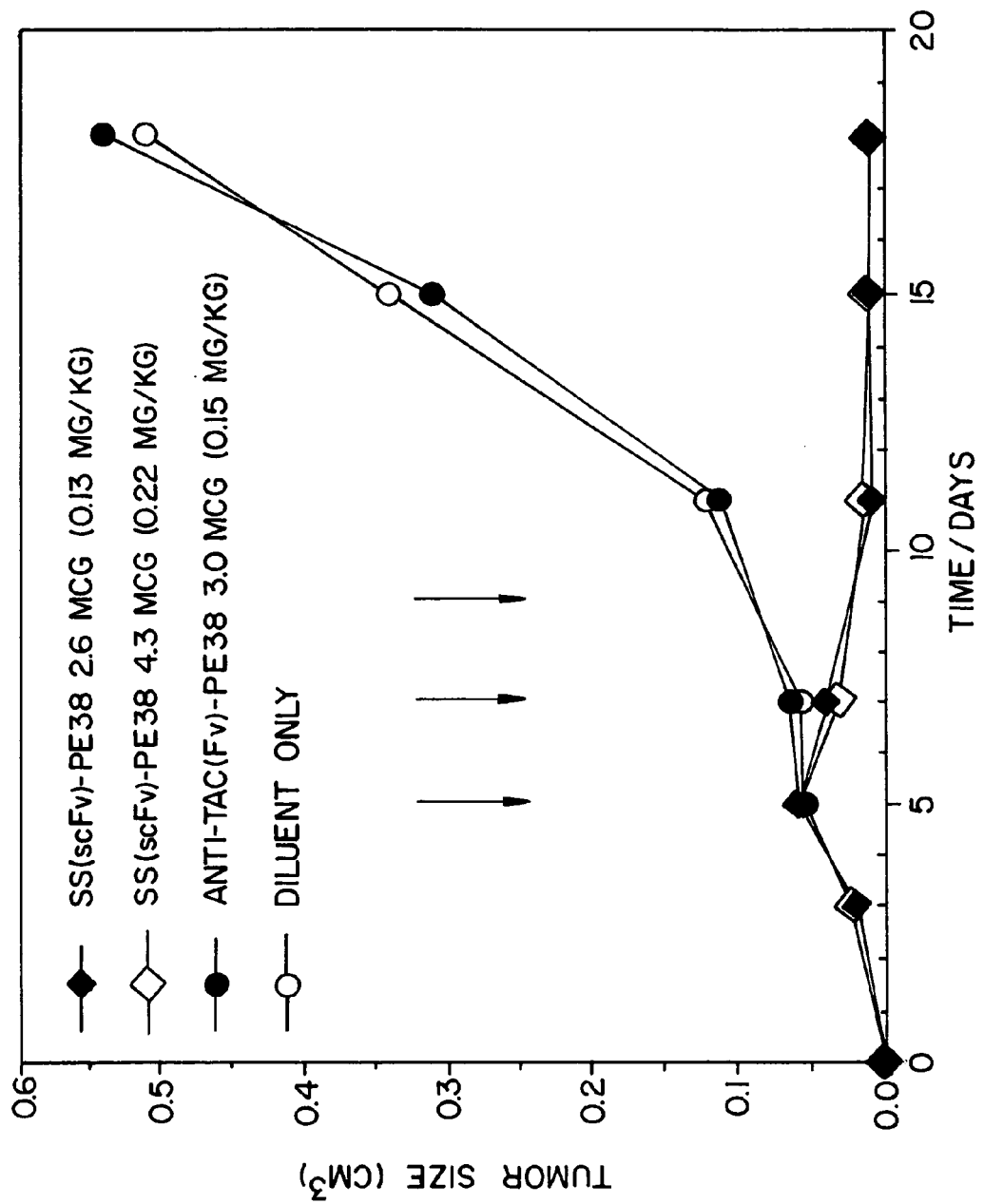
FIG. 5.

FIG. 5 indicates that unlike the control groups, in both dosage treatment groups of mice, tumor regression was observed.

All publications and patents mentioned in this specification are herein incorporated by reference into the specification to the same extent as if each individual publication or patent was specifically and individually indicated to be incorporated herein by reference.

What is claimed is:

1. A method for inhibiting the growth of a malignant cell expressing mesothelin on its cell surface, said method comprising:
   contacting said malignant cell with an effective amount of an immunoconjugate comprising a therapeutic agent attached to an anti-mesothelin antibody having six complementarity determining regions (CDRs), which CDRs have the sequences shown for the respective CDRs set forth in FIG. 1 and which specifically binds to cells expressing mesothelin on their cell surface
   wherein said therapeutic agent inhibits the growth of said cell.

2. A method of claim 1, wherein said anti-mesothelin antibody is a single chain Fv (scFv) antibody comprising a variable heavy ($V_H$) region and a variable light ($V_L$) region.

3. A method of claim 2, wherein said $V_H$ region is peptide bonded to said $V_L$ region through a linker peptide.

4. A method of claim 2, wherein the sequence of the variable heavy ($V_H$) region is as set forth in FIG. 1.

5. A method of claim 2, wherein the sequence of the variable light ($V_L$) region is as set forth in FIG. 1.

6. A method of claim 2, wherein said scFv comprises a variable heavy ($V_H$) region and a variable light ($V_L$) region having the sequences shown in FIG. 1.

7. A method of claim 1, wherein said therapeutic agent is a toxin.

8. A method of claim 7, wherein said toxin is a *Pseudomonas* exotoxin (PE) or a cytotoxic fragment thereof.

9. A method of claim 8, wherein said PE is PE38.

10. A method of claim 1, wherein said malignant cell is contacted in vivo.

11. A method of claim 1, wherein said malignant cell is selected from the group consisting of a mesothelioma cell, an ovarian cancer cell, a stomach cancer cell and a squamous cell cancer cell.

* * * * *